United States Patent
Hisanaka et al.

(10) Patent No.: US 6,544,625 B2
(45) Date of Patent: Apr. 8, 2003

(54) FLEXIBLE SHEET USED FOR DISPOSABLE SANITARY ARTICLE

(75) Inventors: Takayuki Hisanaka, Kagawa-ken (JP); Koichi Yamaki, Kagawa-ken (JP); Miou Suzuki, Kagawa-ken (JP); Hisashi Takai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/748,887

(22) Filed: Dec. 27, 2000

(65) Prior Publication Data

US 2001/0005540 A1 Jun. 28, 2001

(30) Foreign Application Priority Data

Dec. 27, 1999 (JP) .......................................... 11-371480

(51) Int. Cl.$^7$ ................................................. A61F 13/15
(52) U.S. Cl. ...................... 428/131; 428/137; 428/138; 604/378; 604/383; 604/385.01
(58) Field of Search ................................. 428/131, 132, 428/137, 138; 604/365, 366, 370, 371, 374, 378, 383, 385.01, 385.101

(56) References Cited

U.S. PATENT DOCUMENTS

| | | | |
|---|---|---|---|
| 4,637,819 A | * | 1/1987 | Ouellette et al. ............ 428/131 |
| 5,891,119 A | * | 4/1999 | Ta et al. ...................... 604/365 |
| 6,117,524 A | * | 9/2000 | Hisanaka et al. ............ 428/131 |

FOREIGN PATENT DOCUMENTS

| | | | | |
|---|---|---|---|---|
| EP | 0919212 A2 | * | 6/1999 | ........... A61F/13/15 |
| JP | A 62-57551 | | 3/1987 | |

* cited by examiner

*Primary Examiner*—Harold Pyon
*Assistant Examiner*—Alicia Chevalier
(74) *Attorney, Agent, or Firm*—Butzel Long

(57) ABSTRACT

A flexible sheet for disposable sanitary article includes a plurality of aperture-arrays each having a plurality of apertures, a plurality of plane regions arranged so that each pair of the adjacent plane regions have one of the aperture-arrays therebetween and a plurality of regions rising on the plane regions along their peripheral edges surrounding the respective apertures to form irregular undulations. The rising regions each defining on both sides, trough regions having a depth of at least 0.01 mm which are distributed over the flexible sheet at a density of at least 500/cm$^2$.

6 Claims, 5 Drawing Sheets

FLEXIBLE SHEET USED FOR DISPOSABLE SANITARY ARTICLE

BACKGROUND OF THE INVENTION

This invention relates to a flexible sheet suitable as important stock material for disposable sanitary articles, particularly for disposable body fluid absorbent sanitary articles such as disposable diapers or sanitary napkins.

FIG. 6 in the accompanying drawings is a perspective view showing a soft touch exhibiting microapertured plastic sheet 110 disclosed by Japanese Patent Application Disclosure No. 1987-57551. This plastic sheet 110 is adapted to be used as both the top- and backsheets of disposable diapers and is made by feeding a relatively thin unprocessed plastic sheet onto a wire-mesh belt and is then processing the sheet with high pressure liquid jet streams.

The microapertured plastic sheet 110 is formed on its surface destined to be placed against a wearer's skin with a plurality of cylindrical projections 120 which are formed, in turn, on their tops with microapertures 125. The periheraledge of the microapertures 125 are fringed like petals. The sheet 110 is described as exhibiting a cloth-like touch and a lusterless appearance.

In general, a soft touch exhibited by the plastic sheet used in disposable diapers or sanitary napkins when the sheet comes in contact with the wearer's skin is evaluated on the basis of the soft touch exhibited by woven or nonwoven fabrics made of natural or synthetic fiber.

Taking account of the fact that the plastic sheet of prior art has the cylindrical projections formed at their tops with the microapertures which are fringed along their peripheral edges like petals, certainly a cloth-like soft touch will be obtained as the wearer's skin moves to rub the fringed peripheral edges. However, the cylindrical projections themselves have a stiffness substantially higher than a stiffness of the fringed peripheral edges and it is apprehended that the sheet might be even stiffened rather than being softened by forming the sheet with a plurality of such cylindrical projections. Therefore, it is not easy for the plastic sheet of prior art to exhibit a high softness as offered by woven or nonwoven fabrics.

While the plastic sheet of prior art is described as exhibiting a lusterless appearance since the peripheral edges of the respective microapertures are fringed like petals, outer peripheral surfaces of the cylindrical projections 120 as well as the flat zones defined between each pair of the adjacent cylindrical projections 120, 120 are serious factor that enhance the lustrous appearance of the sheet 110.

SUMMARY OF THE INVENTION

An object of this invention is to provide a flexible sheet used for disposable sanitary articles that exhibits a comfortably soft touch, on one hand, and a surface appearance in which luster is sufficiently alleviated.

According to this invention, there is provided a flexible sheet for a disposable sanitary article. The flexible sheet is made of flexible plastic sheet having top and bottom surfaces and a thickness of 0.001~0.05 mm, said flexible sheet including a plurality of substantially plane regions extending in parallel one to another in one direction each having a width of 0.03~1 mm and a plurality of aperture-arrays intermittently arranged in the one direction, each lying between each pair of the adjacent aperture-arrays, each of the aperture-arrays including a plurality of individual apertures each having a width of 0.07~1 mm and a length corresponding to 1.5 or more times of the width so that the plane regions and the aperture-arrays are alternatively arranged in the direction orthogonal to the one direction. Each pair of adjacent the aperture regions having the aperture-array therebetween are connected to each other by a plurality of bridge regions extending from these adjacent plane regions across the aperture-array. Each of the plane regions is provided at least along a part of its zone defining the apertures extending in the one direction with a plurality of regions rising on a top surface of the sheet so as to form a substantially irregular undulation and a plurality of trough regions each defined between each pair of adjacent the rising regions in the one direction wherein, of the rising regions formed on the flexible sheet, the rising regions defining on both sides thereof the trough regions each having a depth of at least 0.01 mm are distributed at a density of at least 500/cm$^2$.

The flexible sheet according to this invention is provided with a plurality of the aperture-arrays extending in one direction and provided on its upper side with a plurality of the fine and easily deformable rising regions irregularly undulating along the peripheral edges of the respective aperture-arrays at a density of at least 500 rising regions per 1 cm$^2$ so that each of the rising regions defines on its both sides the trough regions having a depth of at least 0.01 mm, respectively. The rising regions distributed at such high density on its upper side give the top surface of the flexible sheet a soft comfortable touch and make the sheet lusterless. These rising regions are effective also to improve the water repellency of the sheet's top surface.

DETAILED DESCRIPTION OF THE PREFERRED EMBODIMENTS

A flexible sheet according to the present invention useful as a stock material for making disposable sanitary articles will be more fully understood from the description given hereunder with reference to the accompanying drawings.

Figure 1:
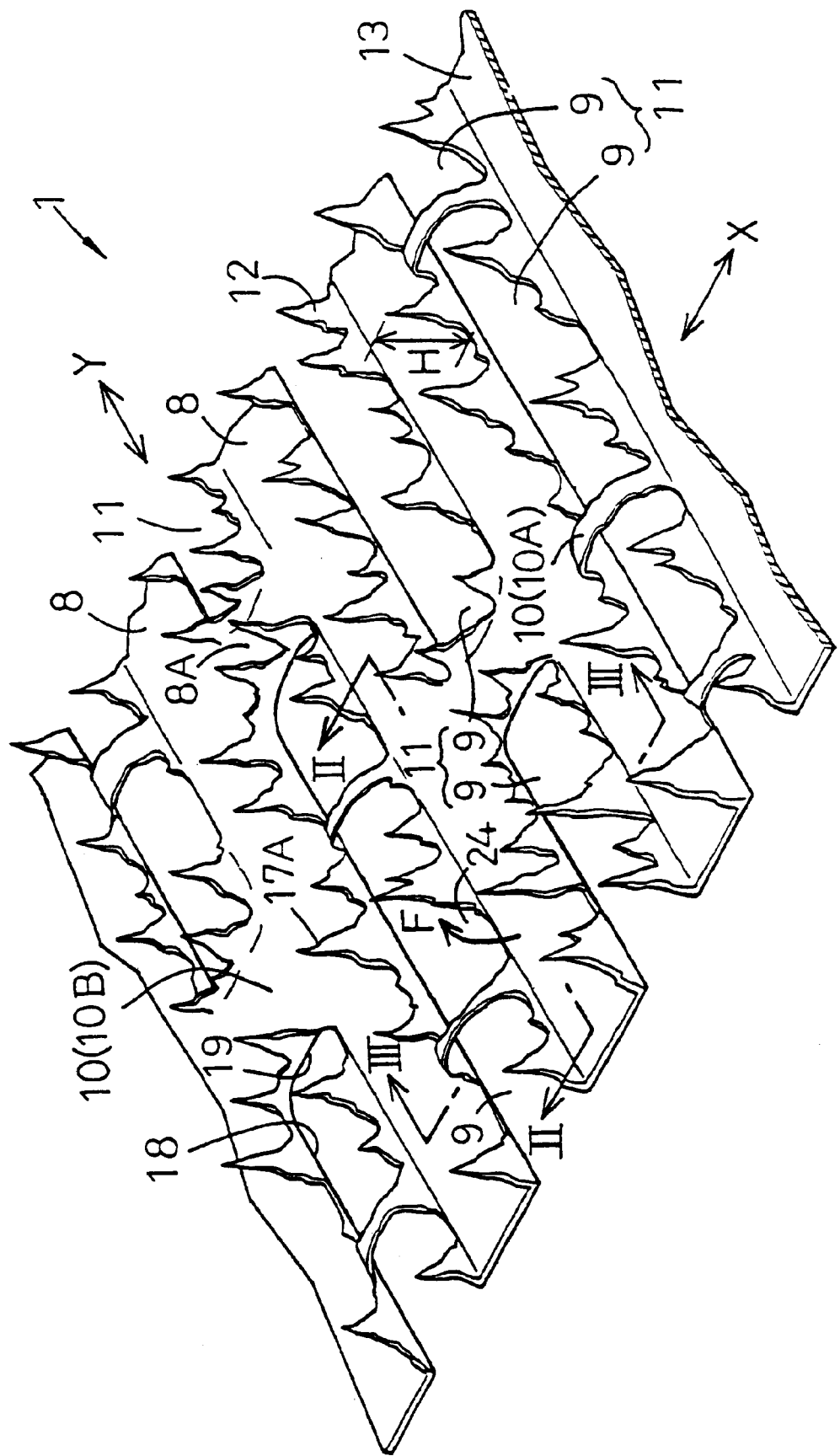
FIG. 1 is a perspective view depicting a flexible sheet according to this invention.

A flexible sheet 1 shown by FIG. 1 in a perspective view comprises a plastic sheet subjected to a process of perforation using high pressure water jet streams having a plurality of substantially plane regions 8 extending in parallel one to another in a direction indicated by a double-headed arrow Y, a plurality of aperture-arrays 11 each defined between a pair of adjacent the plane regions 8, 8 so as to extend in the direction Y and including apertures 9, bridge-like regions 10 extending across the pair of adjacent the plane regions 8, 8 and rising regions 12 formed along peripheral apertures 9 and rising on respective top surface 13 of the plane regions 8. A term "thickness of the flexible sheet 1" used herein should be understood to be a thickness of the plane regions 8 maintaining an initial shape of the plastic sheet.

Figure 2:
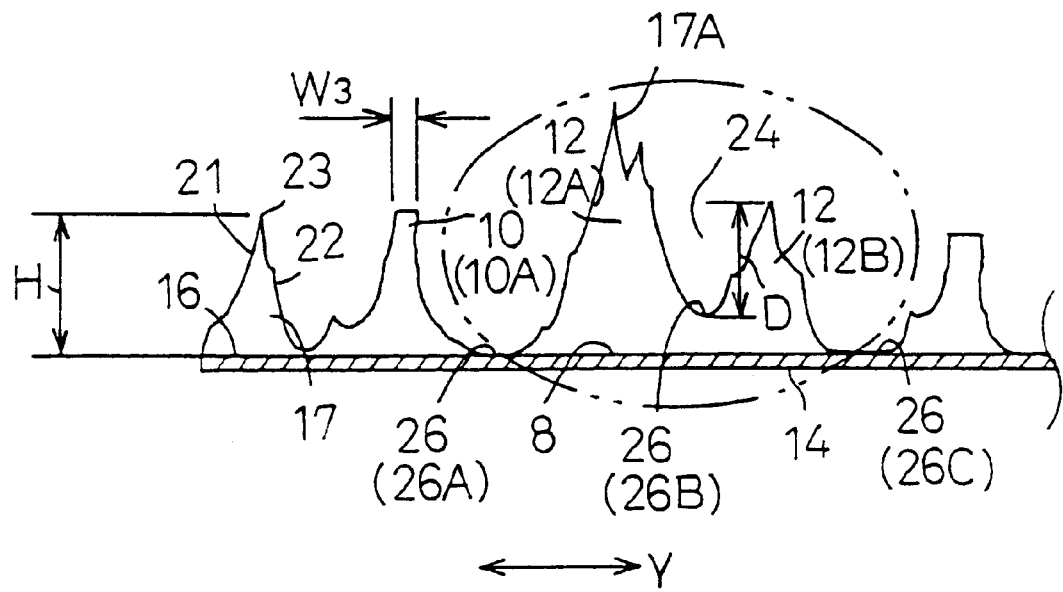
FIG. 2 is a sectional view taken along line II—II in FIG. 1.
Figure 3:
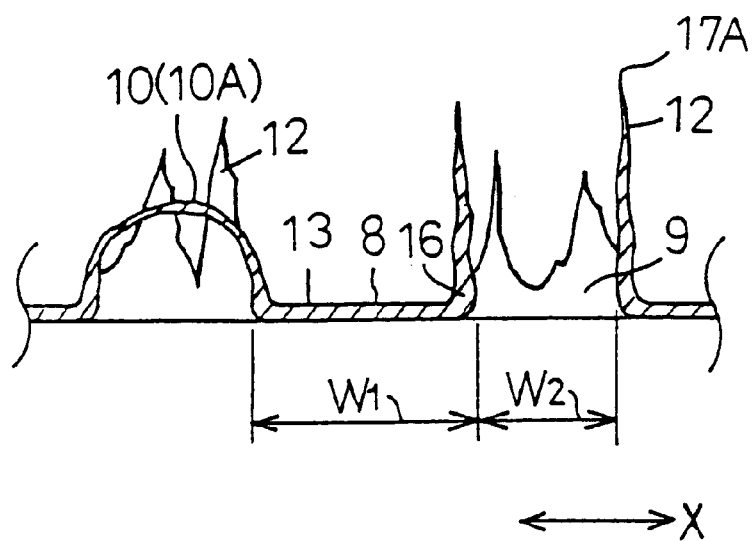
FIG. 3 is a sectional view taken along line III—III in FIG. 1.

FIGS. 2 and 3 are sectional views taken along lines II—II and III—III in FIG. 1, respectively. The plane region 8 of the flexible sheet 1 has a thickness of 0.001~0.05 mm, each pair of respective the apertures 9, 9 are spaced from each other by a width $W_1$ of 0.03~1 mm. A plurality of the apertures 9 are arranged intermittently in the direction Y preferably each having a width $W_2$ of 0.07~1 mm and a length corresponding to 1.5 times or more the width $W_2$. The bridge-like regions 10 extending across the respective aperture-arrays 11 are arranged intermittently in the direction Y and include the bridge-like regions (10A) extending from the top surfaces 13 of the respective plane regions 8 so as to describe circular arcs being convex upward or downward and the bridge-like regions (10B) being as plane as the regions 8. Preferably, each of the bridge-like regions 10 has the minimum width $W_3$ of 0.001~2 mm in the direction Y.

The rising regions 12 are formed by folding partially the plane regions 8 upwardly of the top surfaces 13 along peripheral edges of the respective apertures 9. Each of the rising regions 12 has a thickness being the same as or less than the thickness of the plane region 8. The rising region 12 has a proximal end 16 being contiguous to the plane region 8 and a distal free end 17 being tapered from the proximal end 16 upward. Edges 17 of the distal free ends 17 undulate at least in the directions Y of the direction X and the direction Y. For example, in the embodiment illustrated by FIG. 2, the edges 17A comprise those having oblique sides 21 ascending substantially rightward and those having oblique sides 22 ascending substantially leftward. These oblique sides 21, 22 intersect each other to form pointed apices 23 of the respective rising regions 12. A height H as measured from the top surfaces of the plane regions 8 to the apices 23 is 0.01~2 mm. A trough region 24 is defined between each pair of the adjacent rising regions 12, 12. The trough region 24 has a bottom 26 and a depth D of the trough region 24 corresponds to a vertical distance as measured from the apex 23 to the bottom 26.

Figure 4:
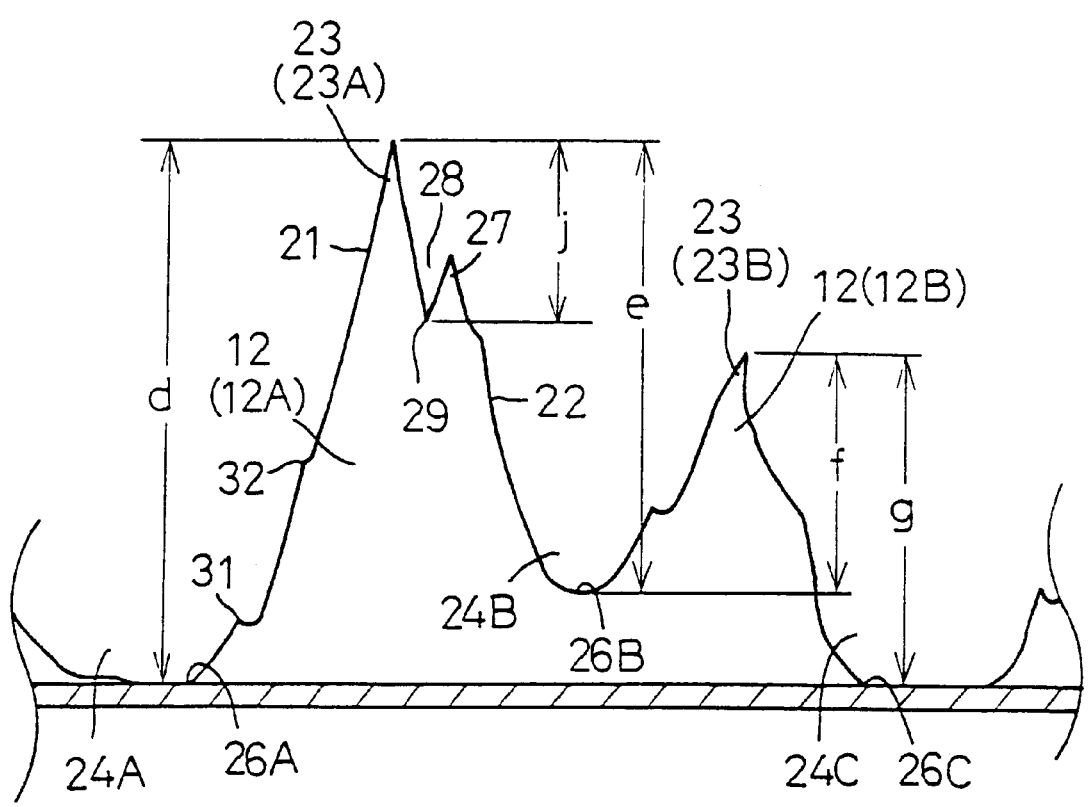
FIG. 4 is a fragmentary view depicting a part of FIG. 2 in an enlarged scale.

FIG. 4 is a scale-enlarged diagram showing a portion of FIG. 2 surrounded by an imaginary line in order to illustrate a manner in which each of the rising regions 12 is defined according to this invention. The rising region 12 herein illustrated comprises a relatively large rising subregion 12A and a relatively small rising subregion 12B wherein the apex 23 of this rising region 12 comprises a first apex 23A of the rising subregion 12B. A first trough subregion 24A is defined on the left side of the first rising subregion 12A, a second trough subregion 24B is defined between the first rising subregion 12A and the second rising subregion 12B and a third trough subregion 24C is defined on the right side of the second rising subregion 12B. The first~third trough subregions 24A~24C have first~third bottoms 26A~26C, respectively. Values of depth D as measured from the first apex 23A to the first and second bottoms 26A, 26B are designated by d, e respectively, and values of depth D as measured from the second apex 23B to the second and third bottoms 26B, 26C are designated by f, g, respectively. These values d, e, f, g should be at least 0.01 mm. The first rising subregion 12A has a leftward ascending oblique side 22 from which a small projection 27 extending upward so that a relatively shallow trough region 28 is defined between the first apex 23A and the projection 27. A value of depth j as measured from the first apex 23A to a bottom 28 of this trough region 28 is less than 0.01 mm. It should be understood that such shallow trough having its depth less than 0.01 mm is not counted as one trough subregion of the trough region 24 defining each of the rising region 12. Similarly, the projection 27 having on its right or left side such shallow trough region 28 is not counted as one rising subregion of the rising region 12. The first rising subregion 12A is counted as one rising subregion inclusively of the associated projection 27 and the trough region 24 defining such first rising subregion 12A should be understood to comprise the first and second trough subregions 24A, 24B formed on both sides of the first rising subregion 12A each having the depth D of at least 0.01 mm. The depth f of the second trough subregion 24B as measured from the second apex 23B of the second rising subregion 12B is also at least 0.01 mm. While the first rising subregion 12A has small projections 31, 32 on its rightward ascending oblique side 21, these projections 31, 32 also are counted as the rising subregions defining the rising region for the same reason as has been described with respect to the projection 27.

Under the definition as has been described above, the flexible sheet 1 is formed with at least 500, preferably 1500 or more rising regions in the average per 1 cm². With a preferable embodiment of the flexible sheet 1, each of the plural plane regions 8 has a substantially uniform width $W_1$ comprises a plurality of the plane regions 8 and each of the plural aperture-arrays 11 also has a substantially uniform width $W_2$. These plane regions 8 and the aperture-arrays 11 alternate in the direction X in FIG. 1 and the rising regions 12 are closely arranged in the direction Y. The number of the rising regions 12 may be counted by observing the sheet 1 along its edge extending in the direction Y as shown in FIG. 2 using a microscope at appropriate magnifications, for example, 100 magnifications. Specifically, the average number P of the rising regions 12 per unit length along the direction Y. The flexible sheet 1 may be observed at the same magnifications along its edge extending in the direction X as shown in FIG. 3 to count the average number q of the aperture-arrays 11 per unit length along the direction X. Two arrays of the rising regions 12 extending in the direction Y are associated with each of the aperture-arrays 11 and therefore a total number of the rising regions 12 of the flexible sheet 1 per unit area can be obtained, so far as the number of the rising regions 12 arranged in the direction X is neglected, from an equation:

$$t = p \times q \times 2.$$

A total number of the rising regions 12 per 1 cm² is given by an equation as will be described.

$$T = p \times (10/2) \times q \times (10/2) \times 2 = p \times q \times 2 \times 25$$

where p and q are the average numbers of the rising regions 12 per 2 mm, respectively. The flexible sheet 1 having a height of at least 0.01 mm and the relatively thin rising regions 12 closely arranged at a high density of 500/1 cm² presents a velvet-like soft touch since the rising regions 12 are easily deformable. These fine rising regions 12 closely arranged and irregularly shaped as has been described above advantageously make the flexible sheet 1 lusterless by diffused reflection occurring on themselves. Furthermore, most of the rising regions 12 are normally kept rising on the top surfaces 13 of the respective plane regions 8 and apt to lean in the direction of the double-headed arrow X thereby to cover the plane regions 8 so that the flexible sheet 1 may exhibit an appearance of rough surface in spite of the presence of the plane regions 8. Consequently, so-called plastic-like luster otherwise exhibited by the plastic sheet is effectively alleviated. Such undesirable plastic-like luster can be further alleviated by adopting the flexible sheet added with grains of titanium oxide, barium sulfate or the like.

The presence of the rising regions 12 closely distributed over the flexible sheet 1 enlarges a contact angle with a drop of water and thereby improves a water repellency of the sheet 1. For example, the sheet 1 made of a polyethylene sheet having a thickness of 7 μm and a contact angle of 99° may be provided with the rising regions 12 at a density of 500 or more per 1 cm² to enlarge the contact angle of the sheet 1 to 105° or larger. This sheet 1 may be used as a breathable water repellent sheet suitable for disposable diapers, sanitary napkins or the like. The inventors measured the contact angle of the sheet 1 using an optical contact angle meter (Model CA—SMII manufactured by KYOWA INTERFACE SCIENCE CO., LTD.).

Figure 5:
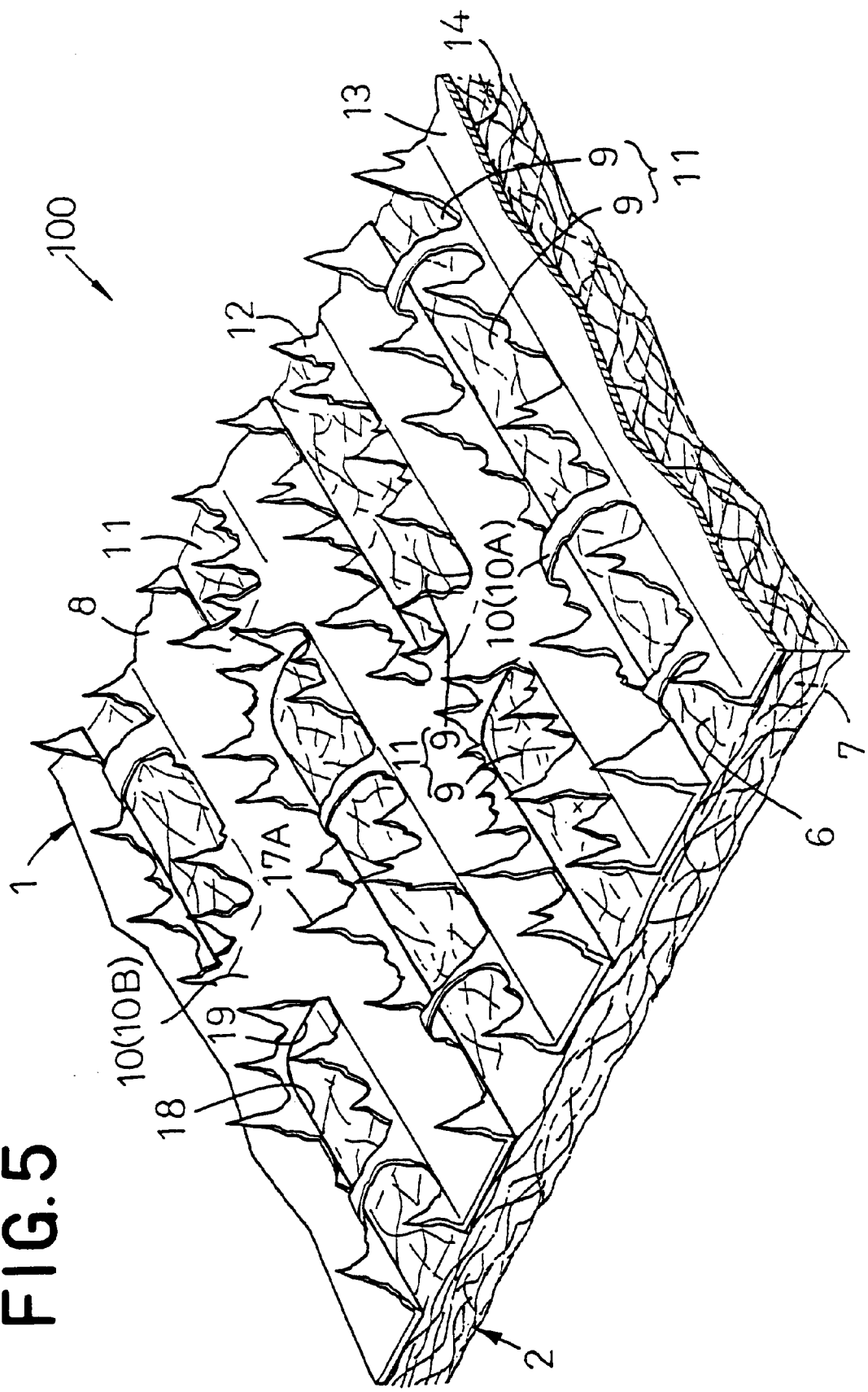
FIG. 5 is a perspective view depicting a composite sheet using the flexible sheet according to this invention.
Figure 6:
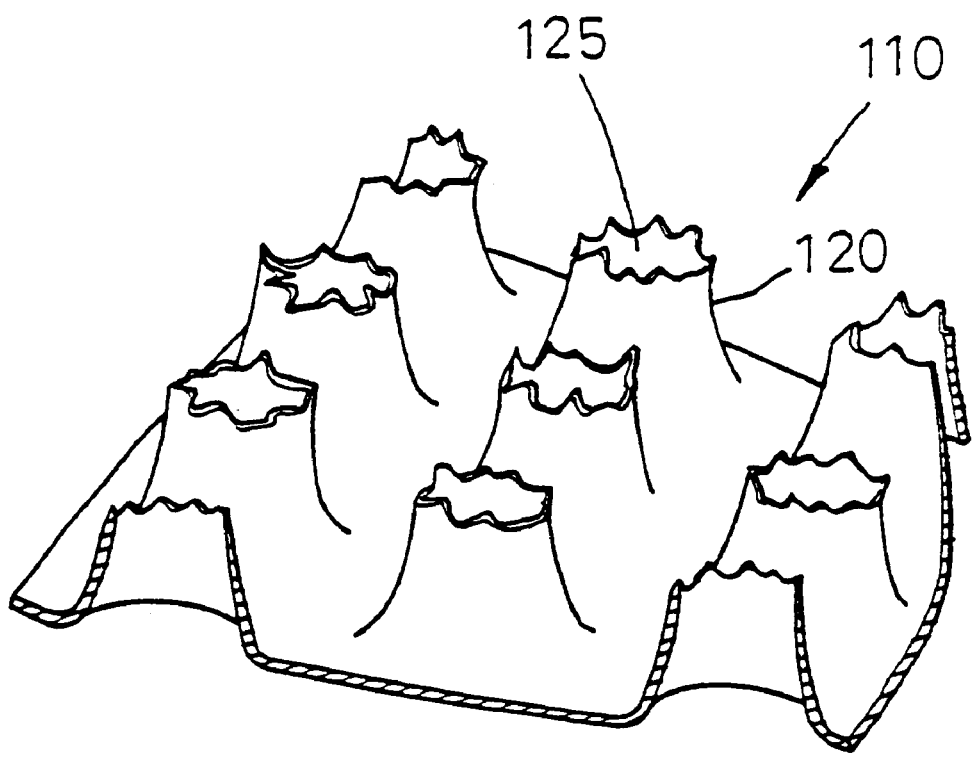
FIG. 6 is a perspective view exemplarily depicting the plastic sheet of prior art.

FIG. 5 is a perspective view showing a composite sheet 100 including the flexible sheet 1 as a component. Since the flexible sheet 1 itself is relatively thin in the plane regions 8 as well as in the rising regions 12, it would be difficult to handle the flexible sheet 1 in the course of a process for making disposable diapers or sanitary napkins if the flexible sheet 1 along is used as the topsheet. One of the characteristics peculiar to the flexible sheet 1 is that the sheet 1 is easily torn along the aperture-arrays 11. This makes it difficult to handle the sheet 1. In addition the flexible sheet 1 is apt to cling to a diaper- or napkin-wearer's skin under the effect of static electricity so that it cannot be easily separated from the skin. To overcome these problems, a fibrous layer 2 maybe bonded to the bottom surface 14 of the flexible sheet 1 as shown so that the flexible sheet 1 may be thickened without impairment of the property expected for the rising regions 12 and at the same time a tear strength of the flexible sheet 1 may be improved. In this way, handling of the sheet 1 is effectively facilitated.

The fibrous layer 2 used for the purpose preferably has a basis weight of 2~100 g/m² is formed form thermoplastic synthetic fibers, chemical fibers such as rayon fibers, a mixture of these synthetic fibers and chemical fibers or a mixture of these synthetic fibers, chemical fibers and natural fibers such as cotton fibers or pulp fibers. Preferably, the fibrous layer 2 is provided in the form of nonwoven fabric made of the suitable types of fibers as have been enumerated above or a mixture thereof and has a desired flexibility. More preferably, the fibrous layer 2 is in the form of nonwoven fabric made of a thermoplastic synthetic fibers having a fineness of 0.1~15 deniers. An example of such nonwoven fabric is nonwoven fabric made of melt blown fibers.

When the composite sheet 100 is used as the liquid-pervious topsheet for disposable diapers or sanitary napkins, it is preferable that the flexible sheet 1 is hydrophilic and the breathability of the composite sheet 100 in the direction of its thickness is in a range of 5~700 cm³/cm²·sec as measured in accordance with JIS(Japanese Industrial Standards)-L-1096 and the water resistance of the composite sheet 100 is in a range of 0~200 mm as measured in accordance with JIS-L-1092. The flexible sheet 1 and the fibrous layer 2 may be bonded together using the technique of heat-or ultrasonic-sealing or suitable adhesive such as hot melt adhesive.

When the flexible sheet 1 alone or the composite sheet 100 is used as the liquid-pervious topsheet for a body fluid absorbent sanitary articles such as disposable diapers or sanitary napkins, body fluids discharged on the articles flows on the respective plane regions 8 in the direction indicated by the arrow Y through each pair of the adjacent rising regions 12, 12 into the apertures 9. For example, body fluids are guided through the trough region 24 into the apertures 9 as indicated by an arrow F in FIG. 1 and then rapidly absorbed by the core. In other words, the rising regions 12 arranged along the peripheral edges of the respective apertures 9 do not cause body fluids to stay on the top surface of the flexible sheet 1 or the composite sheet 100.

The flexible sheet 1 of the composite sheet 100 can be used not only as the breathable water-repellent topsheet of disposable diapers or sanitary napkins but also as a liquid-pervious or water-repellent topsheet for the other article such as training pants, diapers for the incontinent, various pads or gowns used in medical applications. For use as the water-repellent topsheet, the flexible sheet 1 is preferably of hydrophobic nature and the composite sheet 100 preferably includes the fibrous layer 2 made of hydrophobic fibers.

What is claimed is:

1. A flexible sheet for use as a stock material for disposable sanitary articles, which flexible sheet comprises:

a flexible plastic sheet having a thickness of from about 0.001 to about 0.05 mm, a plurality of substantially flat portions having widths of from about 0.03 to about 1 mm and extending in parallel to one another in a first direction, and a plurality of intermittent apertures extending in said first direction between said substantially flat portions so as to form a plurality of aperture rows extending in parallel to one another in said first direction, said plurality of intermittent apertures having widths of from about 0.07 to about 1 mm and lengths of at least 1.5 times the widths thereof;

pairs of said flat portions having said aperture rows therebetween being interconnected by a plurality of bridge portions therebetween and across said aperture rows, said bridge portions extending across the respective aperture rows are formed intermittently in a second direction orthogonal to the first direction, said plurality of bridge portions comprising two types of bridge portions including bridge portions that extend upward or downward from the upper surfaces of the flat portions to the upper surfaces of adjacent so as to describe arcs and those that are flush with the flat portions and said intermittent apertures being defined by edges of said substantially flat portions which extend in said first direction and edges of said bridges portions which extend in said second direction;

said substantially flat portions being formed at least along said edges thereof which extend in said first direction with a plurality of substantially tooth-shaped portions which extend upward from upper surfaces of said substantially flat portions, said tooth-shaped portions defined by alternating peak and trough portions, with a distribution of at least about 500 peak portions per square centimeter that have trough portions on each side thereof, which trough portions have depths of at least about 0.01 mm as measured from a bottom of each trough portion to a apex of an adjacent peak portion.

2. The flexible sheet according to claim 1, wherein apices of said tooth-shaped portions have heights of about 0.01 to about 2 mm above an upper surface of the flexible plastic sheet.

3. The flexible sheet according to claim 1, wherein said flexible plastic sheet is provided on a bottom surface thereof with a fibrous layer having a basis weight of about 2 to about 100 g/m², said fibrous layer being bonded to said bottom surface of said flexible plastic sheet so as to form a composite sheet.

4. The flexible sheet according to claim 3, wherein said fibrous layer comprises hydrophobic fibers.

5. The flexible sheet according to claim 1, wherein said flexible plastic sheet is hydrophobic.

6. The flexible sheet according to claim 1, wherein the distribution of said peak portions is at least about 1500/cm².

* * * * *